United States Patent [19]

Ingersoll et al.

[11] Patent Number: 5,799,386
[45] Date of Patent: Sep. 1, 1998

[54] PROCESS OF MAKING METAL CASTINGS

[75] Inventors: Clyde E. Ingersoll, Tonawanda, N.Y.; Bernt-Roger Gustafsson, Rosersberg, Sweden; Donald B. Kelley, Cleveland, Tenn.

[73] Assignee: Ivoclar AG, Liechtenstein

[21] Appl. No.: 480,695

[22] Filed: Jun. 7, 1995

[30] Foreign Application Priority Data

Oct. 24, 1994 [EP] European Pat. Off. .............. 94250262

[51] Int. Cl.$^6$ .................................................. B21B 1/46
[52] U.S. Cl. ..................... 29/527.5; 164/58.1; 419/37; 419/38
[58] Field of Search ........................ 29/527.5; 419/37, 419/38; 164/58.1

[56] References Cited

U.S. PATENT DOCUMENTS

| 3,961,663 | 6/1976 | Degois et al. ................... 164/58.1 |
| 4,323,395 | 4/1982 | Li . | |
| 5,196,898 | 3/1993 | Ter Maat et al. . | |

FOREIGN PATENT DOCUMENTS

| 559548 | 7/1958 | Canada ................................. 419/37 |
| 1124064 | 2/1962 | Germany .............................. 419/37 |
| 3531017 | 8/1985 | Germany .............................. 419/37 |
| A-35 31 017 | 3/1987 | Germany . | |
| 56-155510 | 12/1981 | Japan ................................... 419/37 |
| 57-188601 | 11/1982 | Japan ................................... 419/37 |
| A-05 042172 | 6/1993 | Japan . | |
| 1726131 | 4/1992 | U.S.S.R. ............................... 419/37 |
| 766186 | 1/1957 | United Kingdom .................. 419/38 |
| 1271157 | 4/1972 | United Kingdom .................. 419/38 |

*Primary Examiner*—Carl J. Arbes
*Attorney, Agent, or Firm*—Nixon, Hargrave, Devans & Doyle LLP

[57] ABSTRACT

A process for making metal castings, comprising the steps of (a) preparing an alloy from at least two different metals;

(b) forming the alloy into a powder;

(c) optionally combining the powder with a lubricant and/or flux;

(d) pressing the powder into pellets;

(e) melting one or more of the pellets;

(f) casting the molten alloy into the mold;

(g) cooling the metal casting.

This process allows for the production of alloy castings even from high melting poorly soluble metals. The use of pellets containing a lubricant and/or flux is preferred. In addition the pellets may contain deoxidizers, grain refiners, and/or oxidizers. The process is especially suitable for the manufacture of dental, jewelry and precision castings.

17 Claims, No Drawings

PROCESS OF MAKING METAL CASTINGS

The present invention relates to a process for making metal castings which comprises the steps of preparing an alloy, forming the alloy into a powder, optionally combining the powder with a lubricant and/or flux, pressing the powder into pellets, melting of the pellets, and casting the molten alloy into the mold.

The production of small metal castings like for example dental or jewelry castings requires that the metal is provided in a form which allows for the easy measurement of the required amount of metal.

Traditionally alloys for casting dental items have been furnished in form of small platelets weighing about 1 to 10 grams. These platelets are prepared by first mixing and melting the metals to make the alloy according to the desired formula, then the molten mixture is poured into a flat bar mold. The so obtained bar is cleaned and reduced in thickness by rolling. This rolling process may include as many as three rolling mills, a break down mill to quickly reduce the thickness, a standard mill to bring the thickness close to the required value, and a finishing mill to give the final reduction and to produce a smooth shiny surface. Most alloys require one or more stress relief heat treatments between the rolling passes to soften them for further rolling. In addition, some alloys require a softening heat treatment of the cast bar. The number of heat treating cycles required depends on the cold working characteristics of the alloy and the thickness of the cast bar. The result of the rolling operation is a long strip of metal several cm wide. The strip may be sheared into several strips of the width required for the finished platelets before chopping it into pieces with the proper weight. These platelets are then used to prepare the desired casting, i.e. a number of the platelets is melted and the molten metal is cast into the mold.

In the early 1930s, nickel and cobalt based alloys were introduced into dentistry. These alloys were not malleable enough to be rolled and chopped and therefore they were furnished in grain form. The grains were formed by pouring the molten alloys into a water bath where the stream of molten metal breaks up into randomly shaped particles. Due to the relative large size of the grains it was difficult to determine the amount of metal for a given casting. Later, uniform pieces were made by casting the alloy into shell molds. The product from the shell mold was either a serrated bar which could be broken at the serratings, or the bar was uniform and cut with abrasive discs to the desired size. These alloys are so strong that unless the serrations are very deep, it is impossible to break them into pieces. Usually, even with serrations, the manufacturer resorts to abrasive cutting to separate the pieces. But even abrasive cutting is difficult and the abrasive cutting discs wear rapidly and are expensive.

Alloys for jewelry use are usually also provided in the form of grains, which are made by the same process as noted above. Some jewelry alloys have also been furnished in the rolled and chopped form.

These procedures for making metal castings are laborious and time consuming due to the numerous steps of rolling and heat treatment. Moreover the equipment needed to produce metal platelets according to the rolling and chopping method is rather expensive and requires a large manufacturing space. DE-OS 35 31 017 discloses a method for preparing alloy castings wherein powders of three or more different metals are mixed and wherein an alloy is formed upon melting of this mixture. The metal powders may optionally be pressed and sintered prior to melting and cast.

This method omits the disadvantages of the above described procedures but it is, however, not applicable to all metals. Thus it is not possible to produce alloys from high melting, poorly soluble metals by the mixed powder method. For example the melting of a mixture of gold and platinum powder does not result in the formation of an uniform alloy suitable for dental purpose, although the binary phase diagrams show that gold and platinum are soluble in all concentrations. The primary problem is that solid platinum is not readily soluble in liquid gold. If the metals are alloyed at temperatures high enough to have both gold and platinum liquid, lower melting metals may vaporize. Moreover this method does not allow the mixing of the metal powders with deoxidizers, grain refiners and any other elements present in less than about 0.5% by weight.

In the production of metal castings it is common to use a reducing or deoxidising flux as a cover for the metals during melting to prevent oxidation at high temperature. A preferable technique is to melt the metal and then add a flux to produce an oxygen barrier and to agglomerate into a slag any oxides coming from the molten metal. Common fluxes are borates, fluorides, silicates, oxides and carbonates but carbon (graphite) flux has also been used (see for example "Skinner's Science of Dental Materials", 9th edition, edited by Ralph Phillips, page 431). In investment casting of small objects it is, however, difficult to measure the correct amount of flux and therefore often poor castings due to too much or too little flux are obtained.

It was therefore desirable to provide a process for the production of metal castings not showing the above disadvantages.

The present invention relates to a process for making metal castings comprising the steps of:

(a) preparing an alloy from at least two different metals;
(b) forming the alloy into a powder;
(c) optionally combining the powder with a lubricant and/or flux;
(d) pressing the powder into pellets;
(e) melting one or more of the pellets;
(f) casting the molten alloy into the mold;
(g) cooling the metal casting.

This method does not show the disadvantages of the procedures known from the prior art. It allows the production of alloy castings even from high melting poorly soluble metals. In a preferred embodiment the pellets produced in step (d) contain an optimum amount of lubricant and/or flux and thus the problems encountered with the use of too much or too little flux are omitted.

The production of alloys from pure metals is accomplished by procedures well known to those skilled in the art. For example platinum and gold are best formed into an alloy by induction melting.

In a preferred embodiment of the present invention a deoxidizer is added to the alloy. The function of a deoxidizer is either to remove oxygen from metal oxides or to move metal oxides into a slag layer. Preferred deoxidizers are lithium, calcium, sodium, zinc and potassium. The deoxidizer is preferably added in a concentration ranging from 0.01 to 3.0% by weight. A concentration of 0.025% by weight is more prefered. Most prefered is the use of 0.025% lithium. It is further preferred that some of the deoxidizer, preferably about 0.005 to 0.05, most preferably 0.01% by weight remains in the alloy after pouring and powder formation. Such small amounts of deoxidizer have been found beneficial in steps (e) and (f) of the present process and may eliminate the need for a flux added by the technician who does the melting and casting.

To obtain a uniform distribution of such small amounts of deoxidizer in the melt it is preferred to prealloy the deoxidizer with other metals. Silver is used to prealloy the deoxidizer for use with gold alloys and palladium for use with palladium or platinum alloys. An especially suitable prealloy contains 95% by weight base metal and 5% by weight deoxidizer; e.g. 95% silver and 5% lithium. To be effective the deoxidizer or the corresponding prealloy has to be added into the melt just before pouring.

It is also preferred to add a grain refiner to the alloy. The grain refiner acts as a nucleating agent during solidification to start large numbers of grains (crystals) growing so that the solid alloy is made up of microscopic grains. To be an effective grain refiner an element must have a very high melting temperature and/or be relatively insoluble in the matrix of the alloy. The grain refiner nuclei must be on the order of atomic size to be effective and to have the quantity of nuclei required.

It was found that ruthenium and/or rhenium are effective in gold, silver and palladium based alloys.

The preferred concentration for the grain refiner is from 0.01 to 3.0% by weight. A concentration of 0.01 to 0.1% is more preferred. A concentration of about 0.025% by weight is most preferred.

To obtain a uniform distribution of the grain refiner in the melt it is preferred to use prealloys. The preferred metal for the formation of prealloys for use with gold, silver and palladium alloys is palladium. Prealloys may be 5% by weight ruthenium and/or 5% by weight rhenium, the balance being palladium.

Alloys for the porcelain fused to metal technique preferably also contain an oxidizer to form an adherent oxide for the porcelain to bond to. Such oxidizers include typically elements like iron, indium, and tin and are preferably added in an amount of from 0.01 to about 3%, more preferably 0.5 to 3% by weight.

Preferred alloys are gold-based dental alloys such as:

Alloy A

| metal | percentage by weight |
| --- | --- |
| gold | 74% |
| silver | 12% |
| palladium | 4% |
| copper | 9% |
| deoxidizers and grain refiners | 1% |

Platinum containing gold-based dental alloys such as:

Alloy B

| metal | percentage by weight |
| --- | --- |
| gold | 84.0% |
| silver | 1.5% |
| platinum | 7.0% |
| palladium | 5.5% |
| deoxidizers, oxidizers grain refiners | 2.0% |

Palladium based dental alloys such as (U.S. Pat. No. 5,174,954):

Alloy C

| metal | percentage by weight |
| --- | --- |
| palladium | 81.95% |
| gallium | 6% |
| indium | 3.5% |
| tin | 3.5% |
| gold | 2.5% |
| silver | 2.5% |
| deoxidizers and grain refiners | 0.05% |

Silver based dental alloys such as (U.S. Pat. No. 3,929,475):

Alloy D

| metal | percentage by weight |
| --- | --- |
| silver | 71% |
| palladium | 25% |
| grain | 4% |

Nickel-based dental alloys such as:

Alloy E

| metal | percentage by weight |
| --- | --- |
| nickel | 77.5% |
| chromium | 12.5% |
| molybdenum | 4% |
| aluminium | 3.5% |
| beryllium | 1.7% |
| silicon | 0.8% |

Cobalt dental based alloys such as:

Alloy F

| metal | percentage by weight |
| --- | --- |
| cobalt | 56% |
| chromium | 25% |
| gallium | 7.5% |
| tungsten | 5% |
| niobium | 3% |
| molybdenum | 3% |
| deoxidizers and grain refiners | 0.5% |

Alloys used in jewelry such as (14 karat):

Alloy G

| metal | percentage by weight |
| --- | --- |
| gold | 58.5% |
| silver | 8.5% |
| copper | 29% |
| zinc | 4% |

Platinum, gold and/or nickel based alloys are most preferred.

The nickel based and cobalt based alloys (alloys E and F) are also suitable for precision casting.

The alloy of step (a) is formed into particles (powder) by means of atomization, mechanical means, grinding, ball milling or other methods, atomization being preferred.

For producing metal powders by atomization commercially available atomizers like for example the HERMIGA MINI 75/3 VI Atomiser, produced by PSI Ltd, Polegate, UK, may be used. The principle of this procedure is, that a flow of the liquid metal is directed into a chamber where it is dispersed by fluid jets directed at the stream of molten metal. The fluid may be gas or water. The shape and size of the particles produced varies with the alloy, the cooling and/or dispersing fluid and the temperature of the melt as well as the design of the atomizer.

When water is the atomizing fluid, the particle shape is quite dependent on the alloy composition. The non-noble alloys tend to scale or rod or other non-uniform shape. Noble alloys tend to spherical shapes. When gas is used as atomizing fluid, most alloys tend towards sphericity.

For compaction into pellets, the irregular shapes and a complete range of particle sizes are preferred. The maximum and minimum particle sizes are of little importance, however, particles below 5 µm tend to become completely oxide in nickel and cobalt base alloys. Particles above 300 µm, preferably above 150 µm, may be screened out because they may interfere with particle flow during pressing of the pellets and result in a poor finish of the surface of the pellets. For this reason alloy particles which are from 5 to 300 µm, especially from 5 to 150 µm, in size are preferred.

When water is used for the atomizing or the final quenching step the powder has to be dried. The drying should be performed under the least oxidizing conditions possible and is preferably done in a vacuum oven.

In a preferred embodiment the alloy powder is mixed with a lubricant and/or flux before the pressing step.

The use of lubricants in the production of green bodies is well known metal powder technology. The lubricant performs two functions in pressing, one is to facilitate the powder particles to move relative to each other so that they can seek the position of greatest density with the least pressure, the other function is to lubricate the mold parts so metal-to-metal contact with its tendency to gall is avoided.

Suitable lubricants comprise waxy fatty acids such as stearic, oleic, linoleic acid as well as their alkali or alkaline earth metal salts. Preferred lubricants are the stearates, oleates and/or linoleates of sodium, potassium, lithium, zinc, calcium and/or magnesium. Stearic acid, and stearates like calcium stearate, lithium stearate and sodium stearate are most preferred. Mixtures of different lubricants may be used.

The amount of lubricant added ranges between about 0.25% and 1% by weight, preferably from 0.3% to 0.7% of the amount of metal. The use of a lubricant results in a prolonged die life, too much lubricant results, however, in excessive smoke during melting and may leave carbon to be incorporated into the alloy. This problem is encountered especially while using palladium, nickel, and cobalt based alloys.

The function of a flux is to provide oxidation protection and remove unwanted oxides. The burning (oxidation) of organic or carbon components of the flux provides a protective atmosphere. The flux combining with oxides in the melt produces a low melting glass which forms a protective layer over the molten metal. The use of fluxes is common in melting and casting of metals and alloys in any size melt, but many fluxes for large melts do not have an organic or carbon component. The lubricant may also perform a flux action by providing a protective atmosphere when it burns out during the melting operation.

When using conventional metal particles the flux has to be added separately by the technician preparing the casting. One of the problems encountered in investment casting of small objects is the use of too much or too little flux. Too much flux results in flux being carried into the mold, too little flux allows the formation of oxides during the melting. As a result pits or other defects in the restoration are formed in both cases. With certain alloys inclusions in the castings, or unwanted components in the alloy result from catalytic decomposition of the flux.

Too much flux is a problem mostly with high noble alloys where there is little oxidation potential, catalytic reduction of flux is encountered especially with palladium alloys.

For non-precious alloys the added flux makes the pellets melt down into a pool whereas the presently furnished metal pieces remain in essentially the same shape because the molten alloy is trapped within an oxide envelope. This envelope makes it much more difficult to determine when the alloy is ready to cast into the mold.

Suitable fluxes comprise borates, phosphates, fluorides and silicates. Preferred fluxes are the oxides or hydroxides of alkali or alkaline earth metals, especially the oxides and hydroxides of sodium, potassium, lithium, zinc, calcium, magnesium as well as mixtures thereof.

Fluorides actively dissolve oxides, whereas other fluxes produce a glass which is protective in not allowing air to contact the hot or molten alloy.

Another group of preferred fluxes are alkali or alkaline earth metal salts of fatty acids. More preferred are the stearates of lithium, sodium, calcium, and/or magnesium, calcium stearate is most preferred. The advantage of this group of fluxes is that they simultaneously act as lubricants and therefore the use of these compounds as lubricant/flux is preferred.

For very high noble alloys fatty acids, especially stearic acid may be sufficient as fluxes.

The metal powder, lubricant and/or flux are mixed by ball milling or other means. When a lubricant and a flux are used together or when mixtures of different lubricants and/or fluxes are used, these compounds are usually mixed first and then this mixture is combined with the metal powder.

The amount of flux used is dependent upon the alloy it is to be used with as well as the kind of flux. Generally 0.06 to 5.5% of the flux are added to the metal powder. For high noble alloys the amount of flux is closer to the lower limit of the above given range, preferably about 0.06%, and for nickel-chromium alloys the amount of flux is closer to the upper limit, preferably about 4.1%. The percentages are by weight of the metal.

In the prior art nickel-based alloys are melted normally without a flux since none of the fluxes known in the art are suitable to prevent the oxidation of the nickel during melting and casting, i.e. the oxide envelope around each particle remains. This is a problem especially in case of small particles as found in metal powders since in this case the oxide in the envelope provides a considerable portion of the total metal.

It has further been found that the combination of an alkali or alkaline earth metal salt of a fatty acid with an alkali or alkaline earth metal oxide or hydroxide exhibits synergism. With nickel based alloys, where this effect is most prominent, the metal fatty acid salt plus a metal hydroxide or oxide causes "clearing" of the melt with less total material than when the metal fatty acid salt or metal hydroxide or oxide are used separately. Even the combination of a free fatty acid and an alkali or alkaline earth metal oxide is much less active than the combination of a fatty acid salt with a alkali or alkaline earth metal oxide. The same effect is observed with other highly oxidizable alloys like for example cobalt based alloys.

The ratio of the metal salt of the fatty acid to the metal oxide and/or hydroxide is preferably from 1:3 to 1:8 on a weight basis. Most preferred is a range of 1:3 to 1:5. It is preferred that the fatty acid metal salt and the metal oxide or hydroxide are based on the same metal.

The mixture of the fatty acid salt and the oxide and/or hydroxide is combined with the alloy powder in a ratio which is from 3.5% to 5.5%, preferably, 4% to 5%.

The preferred fatty acid salts for use with nickel based or other highly oxidizable metal alloys are stearates, lithium, calcium and magnesium are the preferred metals. Mixtures of calcium stearate and calcium hydroxide or lithium stearate and lithium hydroxide are most preferred. Mixtures of metal salts of different fatty acid are also suitable. For nickel based alloys either an addition of 0.5% calcium stearate and 4% of calcium hydroxide by weight based on the amount of metal or 4.5% of a 1:3 ratio mix is most preferred.

The metal/lubricant/flux mixture is formed into pellets by filling it into a suitable form and pressing. For experimental work, a single cavity mold in a hydraulic press may be used. For production quantities, a multistation tablet press such as is used to make medical tablets or powder metallurgy small parts may be used. The pressure required depends on the deformation characteristics of the metal, the friction coefficient between particles and between particles and mold, the particle shape and distribution of particle sizes and other variables known to those skilled in the art of pressing powder metals to desired shapes.

For the purpose of this invention, pressures were determined empirically and preferably range from about 140 bar for very malleable alloys such as high gold alloys to about 300 bar for high elastic modulus alloys such as cobalt-chromium alloys. A preferred pressure range for nickel and cobalt alloys is 200 to 270 bar. Without lubricant, these values are significantly higher.

The pressures used may vary from those listed because the object of the pressing is not to obtain maximum density as required for powder metallurgy parts; only enough pressure to produce a green strength sufficient to withstand shipping and handling is required. Pellets made in this manner may be broken into pieces if required.

Pressing at elevated temperatures can reduce the required pressure, but the complications of heating the pressing machine and molds would be more costly than using higher pressure. In any case, temperatures high enough to produce sintering in the pellets could not be readily accomplished.

Sintering of the pellets is furthermore not required and in a preferred embodiment the pressing is performed at room temperature without sintering.

The metal powder may be formed into any desired shape, although a simple cylindrical shape is least costly for tooling. The maximum dimension of the shape is governed by the size of the entry port of certain casting machine crucibles which are relatively common in dental laboratories. This maximum dimension should be kept to less than about 9 mm. The thickness is governed by the amount of powder required to produce standard pellet weights which are usually in the range of from 1 g to 3 g. The thickness of a pellet will vary with the alloy density; e.g. high gold alloys have densities in the 17 g/cm$^3$ range while nickel alloys have densities in the 8 g/cm$^3$ range.

The pellets obtained can be melted by conventional methods, depending on the casting temperature of the alloy, such as gas/oxygen, gas/air, or induction melting and poured by static or dynamic means into a prepared mold to form the desired configuration of prosthesis or other item. The melting may be conducted in ambient or protective atmosphere, or vacuum. Suitable melting and casting procedures are well known to those skilled in the art.

The process of the present invention allows for a better precision in obtaining the proper weight of alloy for the dental, jewelry and precision casting.

It also allows for the easier and cheaper production of metal castings than conventional processes and even castings made from alloys which are not malleable enough to be rolled to the thinness required for the rolling and chopping method as well as high melting or poorly soluble metals can conveniently be formed.

The pellets prepared according to the process of the present invention are easier to handle than conventional platelets and grains and the labor in producing small castings is reduced.

In a preferred embodiment the pellets contain an optimal amount of flux and as a consequence the technician does not need to add flux during melting, thereby saving labor and avoiding the above mentioned problems encountered with the use of too much or too little flux. As a result a better average quality of the castings is achieved especially in the case of nickel based and other highly oxidizable alloys.

EXAMPLES

Example 1

Preparation of Calcium stearate

Calcium stearate is preferably prepared by melting stearic acid and adding calcium hydroxide or calcium oxide, preferably the hydroxide, in a stoichiometric ratio of 88.5% stearic acid and 11.5% calcium hydroxide. The oxide or hydroxide is added slowly so that the evolving gases do not cause the mixture to boil over. After the addition is complete, the mix is kept hot until steam and gas bubble evolution has stopped. The liquid mix is cooled to a waxy solid which can be pulverized into a powder. Other stearates can be made in the same manner.

Example 2

Gold based dental alloy

A dental alloy is prepared by weighing out separately, the metals listed above, for a gold-based dental alloy (alloy A). The palladium is placed in the bottom of the crucible of an induction melting unit. On top of the palladium, the silver, gold and copper are placed followed by the grain refiner, in this example ruthenium is used in a prealloy with some of the palladium. A gas/air flame is used as a cover to exclude atmospheric oxygen during melting and the induction unit is activated. The power is set to produce a melt in approximately 60 seconds. When the metals are almost completely melted, the zinc is added and when the melt is fully melted, the deoxidizer lithium in a silver base, is added and pouring is done immediately. The pour is made into a tundish (crucible with an orifice in the bottom) where it enters the atomizer. The parameters controlled include the melt temperature at pouring, about 1100° C., the tundish temperature, about 1000° C., the orifice size, 4.5 mm inside diameter, the atomizing water pressure, about 275 bar.

The powder particles are examined by Scanning Electron Microscopy (SEM). The particle shape is mixed flake, sphere, stringers. The particles range from about 6 μm to about 200 μm for those which can be measured. The size distribution appears to be relatively uniform.

Calcium stearate is added in an amount of 0.5% by weight and the metal/stearate mixture ball-milled to achieve good distribution of the lubricant/flux. The powder mix is formed into pellets using a standard Stokes tabletting machine at about 140 bar. The tablets obtained are 9 mm in diameter and weigh about 1.5 grams.

4 tablets are melted and cast into an investment mold to form a 3-unit dental bridge, using standard "lost wax" techniques well known to those skilled in the art. The tablets are easy to handle and to provide the correct amount of metal. The castings are of high quality, not showing any deficiencies due to either high or low amounts of metal or flux.

Example 3

Jewelery Alloy

A 14 k gold jewelery alloy of the composition noted above (alloy G) is atomized in the same manner as the dental alloy given in example 2. The powder particles are examined by SEM. The particle shape is largely spherical. The particles range from about 5 μm to 260 μm. The size distribution appears to be relatively uniform. Calcium stearate is added in an amount of 0.5% by weight and the metal/stearate mixture ball milled to achieve good distribution of the lubricant/flux. The powder mix is formed into pellets using hydraulic press and a single cavity mold to about 140 bar. The tablets obtained are 9 mm diameter and weigh about 1.5 grams. The parameters controlled include the melt temperature at pouring, about 1000° C., the tundish temperature, about 900° C., the orifice size, 4.5 mm inside diameter, the atomizing water pressure, about 275 bar.

5 tablets are melted and cast into an investment mold to form 3 rings, using standard "lost wax" techniques well known to those skilled in the art. The tablets are easy to handle and to provide the correct amount of metal. The rings are of high quality, not showing any deficiencies due to either high or low amounts of metal or flux.

Example 4

Nickel-based dental alloy

A nickel-based dental alloy of the composition given above (alloy E) is prepared according to example 2. The powder particles are examined by SEM. The particle shape is mixed flake, stringers, so varied that no valid particle size can be measured. The size distribution appears to be relatively uniform. Calcium stearate and calcium hydroxide are weighed out in a 1:3 ratio and the mixture ball milled to achieve good blending of a lubricant and flux. The mix is combined with a metal powder at 4.5% of lubricant/flux based on the metal powder weight and again ball milled to get a uniform mix of all components. The powder mix is formed into pellets using a standard Stokes tabletting machine at about 140 bar. The tablets obtained are 9 mm diameter and weigh about 1.5 grams.

9 tablets are melted and cast into investment mold to form the two parts of a furnace fixture for firing dental porcelain onto dental alloys using standard "lost wax" techniques well known to those skilled in the art.

The fixture is made in 2 parts which fit together by projection of one piece fitting into a hole in the other one, the projection and hole forming a hinge. The fit is precise enough that only slight adjustment is required to make the fixture parts work together successfully.

Two more tablets are melted and cast in the same manner to form a 3 unit dental bridge. This metal bridge is then prepared to accept a dental porcelain coating. The dental porcelain coating is successfully fired in place without any problems.

The tablets of this example melt into a pool which casts as a fluid without restriction. In contrast to this, present cut ingots melt, but each ingot is enclosed in an envelope of oxide such that it is doubtful when full melting is accomplished. The molten metal must escape from the envelope to leave the crucible and enter the mold.

Comparative Example 1

A standard cut ingot (nickel-based dental alloy according to example 4) is used to cast a 3-unit bridge as described in example 4. One ingot, 7 grams is too much metal for one casting. An attempt to use flux (calcium hydroxide, unmeasured quantity) results in a glossy coating over the oxide coating, which does not seem to be any less. Measurement of the temperature of the metal is impossible by optical methods due to the oxide coating. The detection of a slight slump and the color change is the means of determining casting temperature. The casting is made but solidification shrinkage occurs in the wrong place due to too much alloy.

Examples 5 to 7

Nickel-based Dental Alloys

Pellets are made as described in example 4, except that

Example 5

0.3 to 0.7% by weight magnesium stearate and 3.0 to 5.0 of magnesium hydroxide are used. When 3 pellets are melted in a crucible each pellet melts and the 3 float together but there is still an oxide film on the surface of the melt (the melt does not clear). The casting is easily accomplished.

Example 6

In another embodiment the powder of example 4 is mixed with 0.3% by weight lithium stearate and 3% by weight calcium hydroxide. Similar results as in Example 5 are obtained.

Example 7

The metal powder of example 4 is mixed with 3% by weight sodium stearate. A melt is achieved but the pellet shapes are still evident because of oxide envelopes. Due to smaller pieces, it is even more difficult to determine when the alloy is melted enough to be fluid for casting, there is no slumping. A casting is made successfully because the oxide coating is less than without flux.

Comparative Example 2

Pellets are made as described in example 4 but no lubricant or flux are used. When it is judged that the alloy within the envelope is melted, casting is attempted. No liquid metal emerges. SEM examination determines that each particle of powder has its own oxide envelope which prevents the liquid metal from escape.

Example 8

Palladium-Based Dental Alloy

A palladium dental alloy is prepared according to the formula given above (alloy C) and atomized as in example 2. A carbon monoxide/air flame is used as a cover to exclude atmospheric oxygen during melting. The melt temperature is about 1400° C., the tundish temperature about 1200° C., the orifice size 4.5 mm inside diameter, the atomizing water pressure about 275 bar.

The powder particles are examined by SEM. The particle shape is primarily spherical. The particles range from about 10 μm to about 270 μm. The size distribution appears to be relatively uniform. Calcium stearate is added in an amount of 0.5% by weight and the alloy/stearate mixture ball milled to achieve good distribution of the lubricant/flux. The powder mix is formed into pellets using a standard Stokes tabletting machine at about 140 bar. The tablets obtained are 9 mm diameter and weigh about 1.5 grams.

3 tablets are melted and cast into an investment mold to form a 3-unit dental bridge, using standard "lost wax" techniques well known to those skilled in the art. Dental porcelain is successfully fired onto its surface.

Example 9

Synergism of Flux Combinations

Pellets were formed according to example 4. As flux 4.5% based on the amount of metal of one of the components or mixtures of components listed below was used. The pellets were heated by torch or by induction until hot enough to melt (by observation) and casting was attempted by centrifugal casting.

Although the same amount of flux was used in each experiment only the use of a mixture of calcium stearate and calcium oxide or calcium hydroxide resulted in a sufficient flux action. These results clearly demonstrate the synergism of mixtures of an alkali or alkaline earth metal salt of a fatty acid with an alkali or alkaline earth metal oxide or hydroxide when used as fluxes in metal casting.

All ratios (stearic acid or stearate to oxide or hydroxide) were 1:3 (by weight) for comparison but other ratios were tried with some combinations to see the result. Little difference was found, where it was tried except lower ratios (less flux) tended to worsen the results.

| flux | results |
|---|---|
| calcium oxide | no apparent effect |
| calcium hydroxide | no apparent effect |
| stearic acid | not enough fluxing action to prevent formation of oxide envelope on each particle |
| calcium stearate | some visible melting together of particles is observed, but metal could not be cast centrifugally |
| stearic acid and calcium oxide | more melting together than with calcium stearate alone, but melting was not complete and only a small amount of fluid metal (less than 25%) escaped from the oxide envelope due to the centrifugal force of the machine |
| stearic acid and calcium hydroxide | more melting together than with calcium stearate alone, but melting was not complete and only a small amount of fluid metal (less than 25%) escaped from the oxide envelope due to the centrifugal force of the machine |
| calcium stearate[1] and calcium oxide | metal powder completely melts together, metal could be cast without any difficulties |
| calcium stearate[2] and calcium hydroxide | metal powder completely melts together and "clears", metal could be cast without any difficulties |

[1] calcium stearate made with calcium oxide
[2] calcium stearate made with calcium hydroxide

We claim:

1. A process for making metal castings, comprising the steps of
   (a) preparing an alloy from at least two different metals;
   (b) forming the alloy into a powder;
   (c) optionally combining the powder with a substance which acts as a lubricant and/or a flux;
   (d) pressing the powder into pellets;
   (e) melting one or more of the pellets to produce a molten alloy;
   (f) casting the molten alloy into a mold; and
   (g) cooling the metal casting.

2. The process according to claim 1 wherein the alloy comprises a metal selected from the group consisting of platinum, gold, palladium, silver, cobalt, and nickel.

3. The process according to claim 1 wherein the alloy additionally comprises a deoxidizer and/or grain refiner and/or oxidizing element.

4. The process according to claim 3 wherein the deoxidizer and/or grain refiner and/or oxidizing element is added in an amount of 0.01 to 3.0% each by weight.

5. The process according to claim 1 wherein the powder is formed by melting the alloy and atomizing the molten alloy.

6. The process according to claim 1 wherein the alloy powder comprises particles ranging from 5 μm to 300 μm in size.

7. The process according to claim 1 wherein the alloy powder is formed by particles of non-uniform shape.

8. The process according to claim 1 wherein the alloy powder is combined with a fatty acid as the substance.

9. The process according to claim 8 wherein the lubricant and/or flux is used in an amount of between 0.06 to 5.5% by weight of the amount of metal.

10. The process according to claim 1 wherein the substance is a mixture having two components, wherein the first component is an alkali or alkaline earth metal salt of a fatty acid and the second component is an alkali or alkaline earth metal oxide or hydroxide.

11. The process according to claim 10 wherein the ratio of the first component to the second component is from 1:3 to 1:8.

12. The process according to claim 10 wherein the mixture is added in an amount of 3.5 to 5.5% by weight of the metal.

13. The process according to claim 10 wherein the mixture is calcium stearate and calcium oxide or calcium stearate and calcium hydroxide.

14. The process according to claim 10 wherein a pressure of 140 to 300 bar is used for the pressing of the metal powder.

15. The process according to claim 1 wherein the pellets have a weight of 1 gram to 3 grams.

16. The process according to claim 1, wherein the alloy powder is combined with an alkali or an alkaline earth metal salt of a fatty acid as the substance.

17. The process according to claim 1, wherein the substance acts as a lubricant and a flux.

* * * * *